United States Patent [19]
Karsdon

[11] Patent Number: 5,964,789
[45] Date of Patent: *Oct. 12, 1999

[54] TRANSCUTANEOUS ELECTRIC MUSCLE/NERVE CONTROLLER/FEEDBACK UNIT

[76] Inventor: Jeffrey Karsdon, New York, N.Y.

[*] Notice: This patent is subject to a terminal disclaimer.

[21] Appl. No.: 09/017,443

[22] Filed: Feb. 2, 1998

Related U.S. Application Data

[63] Continuation of application No. 08/458,293, Jun. 2, 1995, Pat. No. 5,713,946, which is a continuation of application No. 07/996,572, Dec. 24, 1992, Pat. No. 5,447,526.

[51] Int. Cl.[6] .................................................. A61B 17/42
[52] U.S. Cl. ................................................. 607/39; 607/62
[58] Field of Search ................................. 607/39, 40, 41, 607/42, 62, 138

[56] References Cited

U.S. PATENT DOCUMENTS 4,232,680  11/1980  Hudleson et al. ......................... 607/74
5,397,344  3/1995  Garfield et al. ......................... 607/138

Primary Examiner—Scott M. Getzow
Attorney, Agent, or Firm—Hamilton Brook Smith & Reynolds, P.C.

[57] ABSTRACT

A transcutaneous uterine contraction inhibiting device comprises a first plurality electrode positioned on an anterior side of an abdomen of a patient, a second plurality electrode positioned on the anterior side, and an electric current generator establishing electric current flow between the first plurality electrode and the second plurality electrode. The first plurality electrode is positioned above an upper portion of the uterus and extends laterally across the uterus. The second plurality electrode is positioned on a mid to lower portion of the uterus and also extends laterally across it. Further, a feedback unit can be provided for generating a signal indicative of any uterine contractions. The electric current generator then establishes an electric current in response to the signal from the feedback unit.

20 Claims, 10 Drawing Sheets

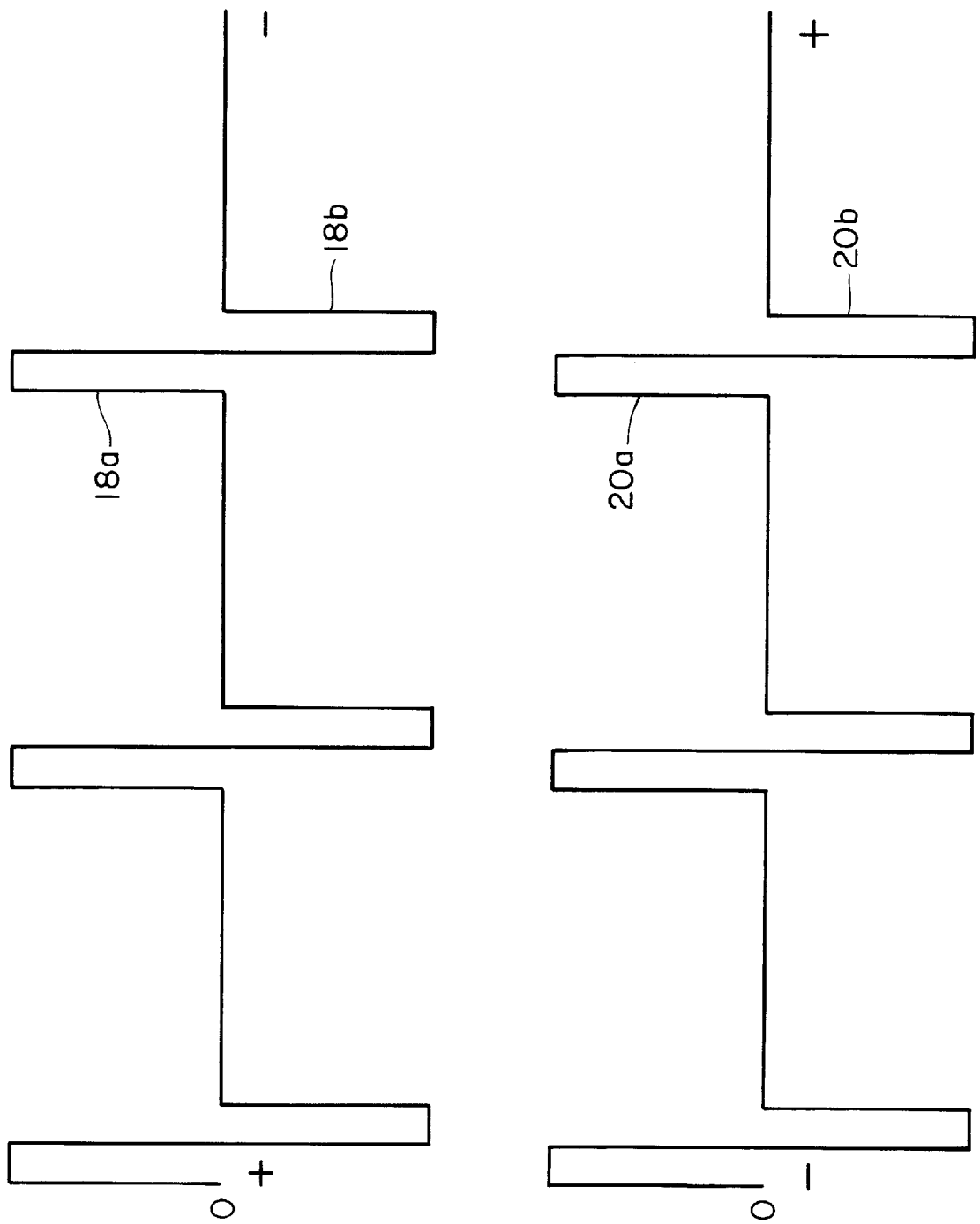

TRANSCUTANEOUS ELECTRIC MUSCLE/ NERVE CONTROLLER/FEEDBACK UNIT

RELATED APPLICATIONS

This application is a Continuation of U.S. Ser. No. 08/458,293, filed Jun. 2, 1995 now U.S. Pat. No. 5,713,940, which is a Continuation application of U.S. Ser. No. 07/996,572, filed Dec. 24, 1992 now U.S. Pat. No. 5,447,526, the entire teachings of which are incorporated herein by reference.

FIELD OF THE INVENTION

The invention relates to transcutaneous electrical control of muscles and/or nerves for either inhibition (decrease) or stimulation (increase) of muscle activity. More specifically, the invention is concerned with but not limited to the control of the uterus as well as other muscles, particularly smooth muscles, to either inhibit contractions, such that the contraction force is decreased, or stimulate contractions, such that contraction force is increased.

BACKGROUND OF THE INVENTION

Electrical apparatuses for transcutaneous, i.e., through the skin, control of muscles and nerves in the human body are generally well known. Such apparatuses are commonly used on striated muscle to treat tissue injury or to control pain. For treatment, injured striated muscles are electrically stimulated to maintain tone, size, and strength. Electrical stimulation can also be used to promote the healing of injured tissue by facilitating the transport of nutrients and release toxins. Pain control is obtained by stimulating the nerve to block out pain.

For muscle injury healing, many types of apparatuses are available. Power muscle apparatuses to maintain striated muscle tone and strength are disclosed in U.S. Pat. Nos. 4,976,264, 4,996,987, and 5,048,522 to Petrofsky. U.S. Pat. No. 5,097,833 to Campos teaches further refinements of the technique by using variations of the pulse forms.

Similar techniques have been disclosed for pain relief: U.S. Pat. No. 4,989,605 to Rossen reverses electrical polarity for pain relief, U.S. Pat. No. 4,938,223 to Charters (1990) varies amplitude to make the treatment more tolerable.

Tissue healing is another application of this technology. U.S. Pat. No. 4,993,413 to McLeod (1991) induces an electrical voltage in tissue specifically bone, and U.S. Pat. No. 4,895,154 to Bartelt (1990) teaches voltage inducement in soft tissue.

The teachings of these prior art devices and methods can be generally summarized as follows. They are generally applied on striated, skeletal, muscle and not smooth muscle. Further, they are used essentially to stimulate or increase activity and tone and not to inhibit or decrease activity and tone since relatively short electrical pulses are used, regardless of the variations in pattern, which tend to stimulate muscle activity. The transcutaneous nerve stimulator, TENS, that stimulate nerves to increase the pain threshold also use relatively short electrical pulses. Again their main focus is not smooth muscle but nerves. Finally, the prior art devices and methods utilize a constant voltage devices even through any effect is dependant on the various tissue resistances encountered

SUMMARY OF THE INVENTION

The present invention is directed towards a transcutaneous apparatus that produces a pulse train of electrical current which overcomes the disadvantages of the prior art because it can be used for smooth muscle. Also the present invention can be used for inhibition of the muscle activity. This invention is a novel way to produce a high therapeutic effect for inhibition or decrease of selected muscle activity with minimal resulting discomfort.

Accordingly, one object is to provide an apparatus that will affect the smooth muscle, including the uterus, in a human or animal body.

Another object is the inhibition or decrease of muscle activity, e.g. contractions and tone.

Still another object is to use relatively long electrical pulses with a plurality of wave patterns which will affect the smooth muscle and not specifically the striated muscle/nerve.

A still further object is to use a controlled constant current output which is a better method of controlling electrical-muscle interaction because it is independent of varying tissue resistance.

Further objects and advantages are to provide an apparatus and method which can be used easily and conveniently to inhibit or decrease smooth muscle contractions of the uterus or other smooth muscles, which will have a constant current output to compensate for variations in the individual tissue impedance, which can also be used to stimulate or increase smooth muscle contractions, which can reverse the electrode polarity for flexibility of maximum effect, which is easy to use, which can have a varied amount of time which the current flows so as to obtain maximum effect with minimal use of energy, which can be used repeatedly, which has a feedback input loop for positive or negative control of the output, and which can diminish the need for the reliance on other methods to modify uterine smooth muscle activity.

BRIEF DESCRIPTION OF THE PREFERRED EMBODIMENTS

Closely related figures have the same number but different alphabetic suffixes.

FIGS. 5A and 5B is a timing diagram of a pulse illustrating reversible electrode polarity and bipolar pulses (positive-to-negative-to-positive) of the invention;

DETAILED DESCRIPTION OF THE DRAWINGS

Figure 1:
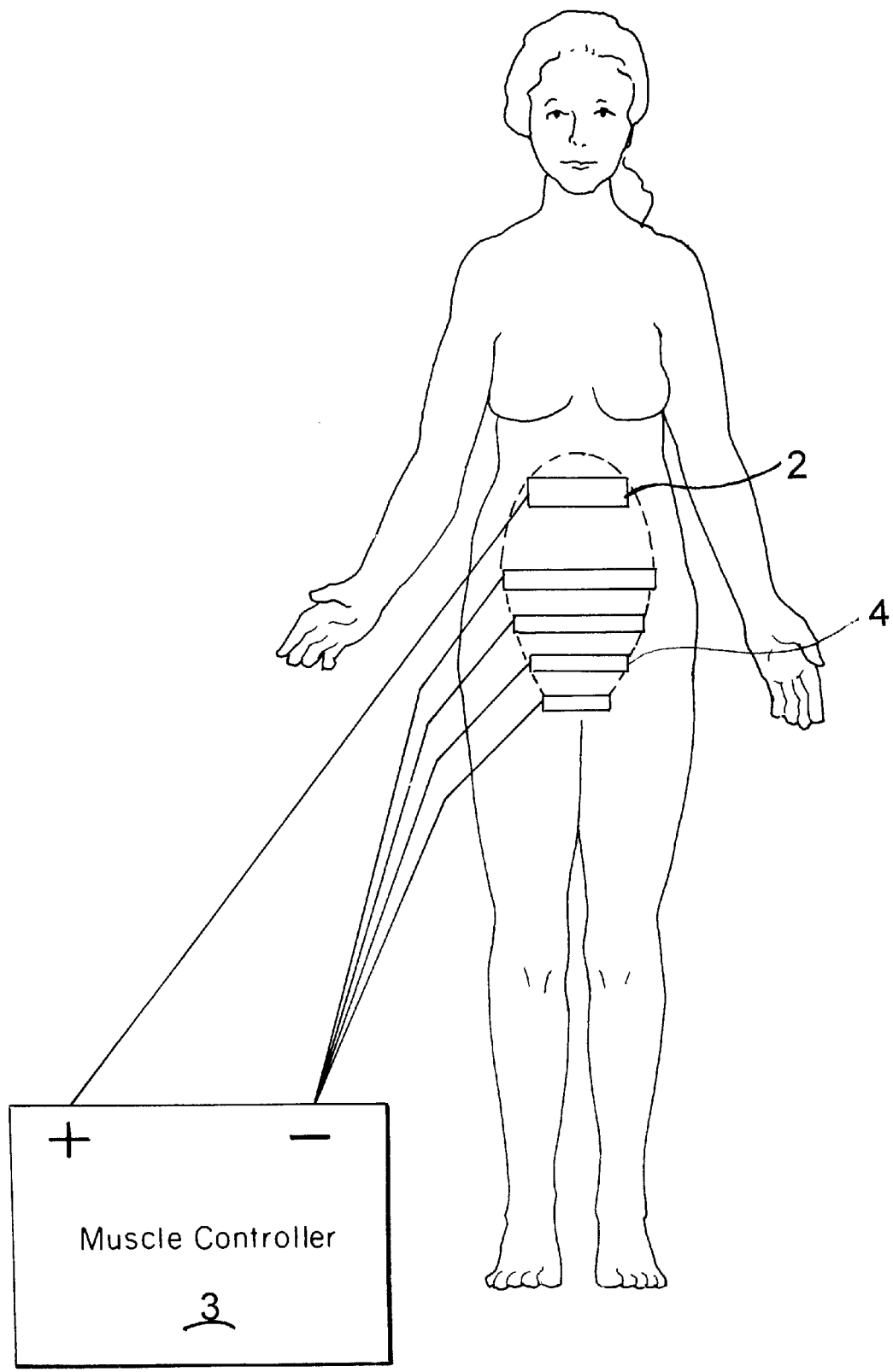
FIG. 1 is a schematic view of the transcutaneous uterine muscle/nerve controller apparatus and electrodes positioned over the uterus of the human body of the present invention.

Turning now the figures, the transcutaneous muscle controller apparatus constructed according to the principles of the present invention is schematically shown in FIG. 1. More specifically, a uterus of a pregnant woman occupies the region indicated by the dotted line 1. A positive electrode 2 of a muscle controller 3 is placed on the woman's abdomen over a top of the uterus. Four negative electrodes 4 are spaced over the lower portions of uterus beginning at approximately a mid portion of the uterus. The negative electrodes 4 and the positive electrode 2 are connected to a muscle controller 3.

Figure 7:
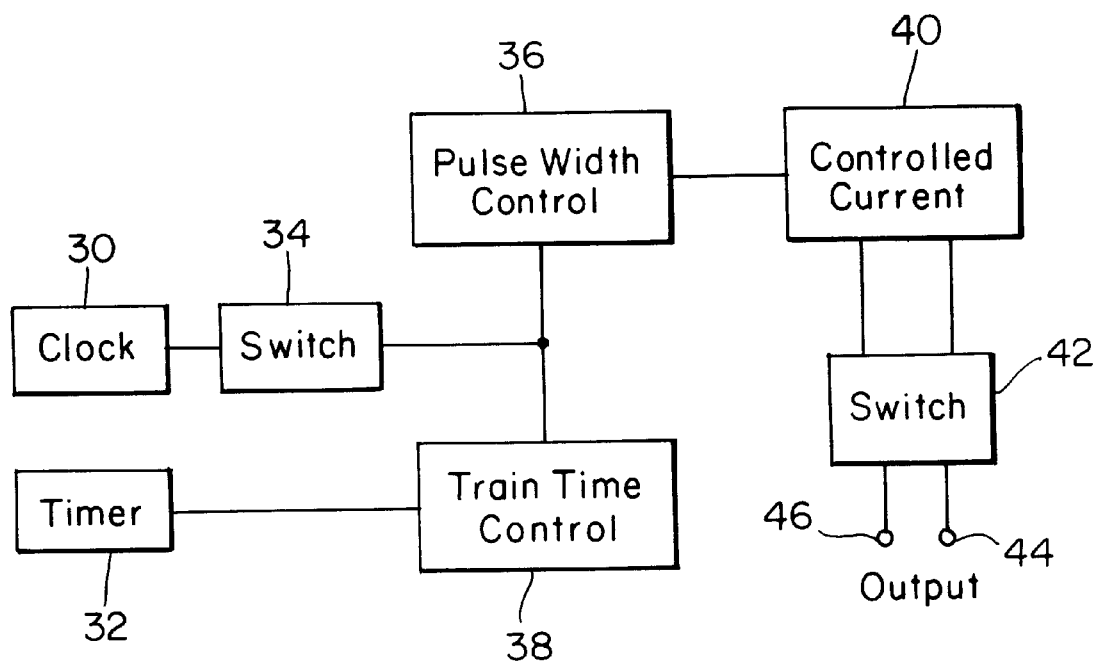
FIG. 7 shows a block diagram of a circuit of the invention for producing the pulses shown in FIGS. 2 to 4.

FIG. 7 is a block diagram of the muscle controller 3 that drives the positive electrode 2 and the negative electrodes 4. Here, a clock 30 connects to a switch 34 which provides for the activation of the controller 3. A timer 32 connects to a train on time control 38 that determines the amount of time that current flows between the electrodes 2,4. The switch 34 connects to a pulse width control 36 and the train on time control circuit 38. The output of the pulse width control 36 is connected to a mono-polar control current unit 40 which connects to a switch 42 for controlling the polarity of the electrodes attached to output terminals 44 and 46. The terminals 44 and 46 are then individually connected to either the positive electrode 2 or the negative electrodes 4.

Figures 2A, 2B:
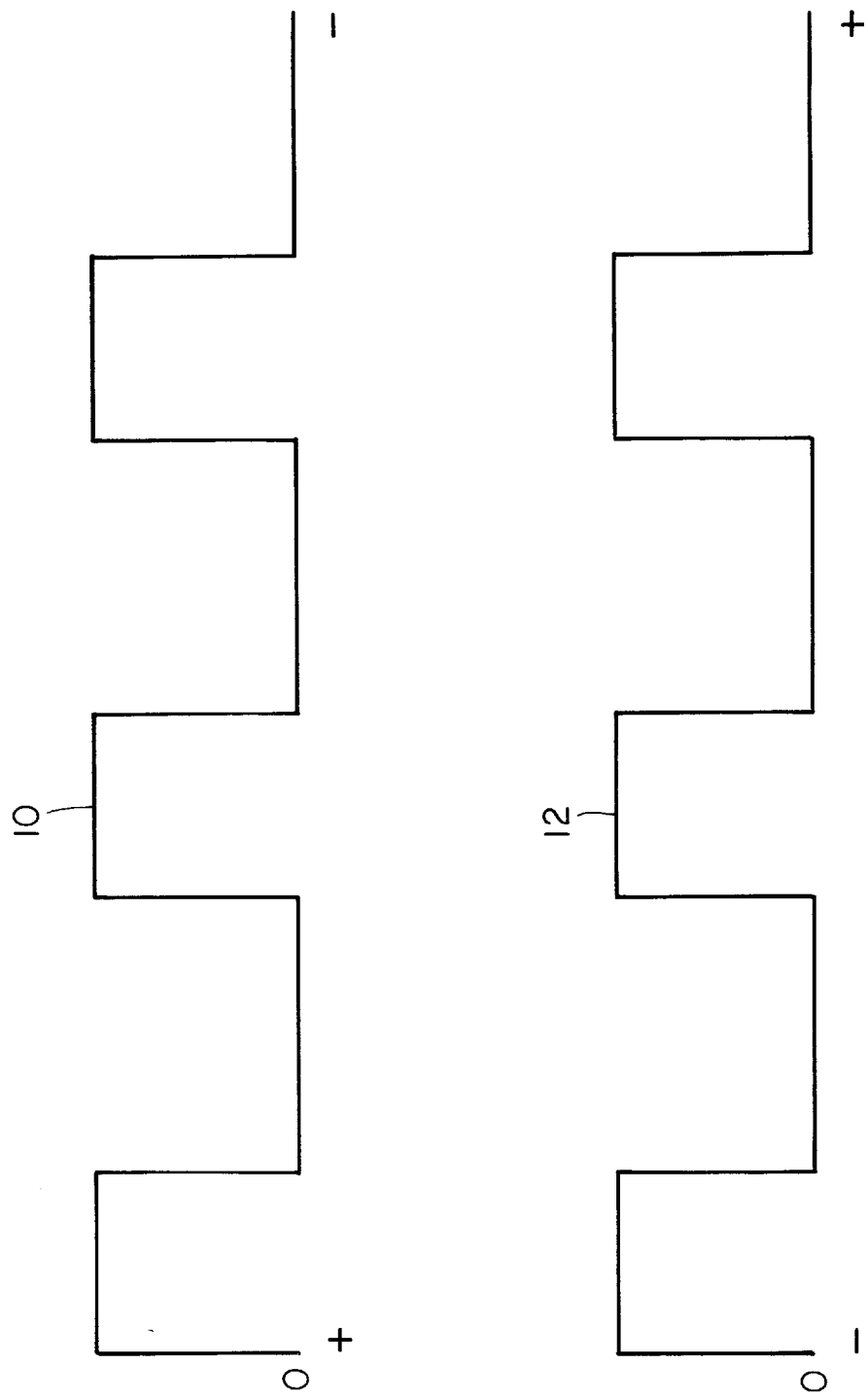
FIGS. 2A and 2B show two monopolar pulse trains with positive and negative polarity and timing demonstrating the inventive reversible positive and negative electrode polarity of the invention.
Figures 3A, 3B:
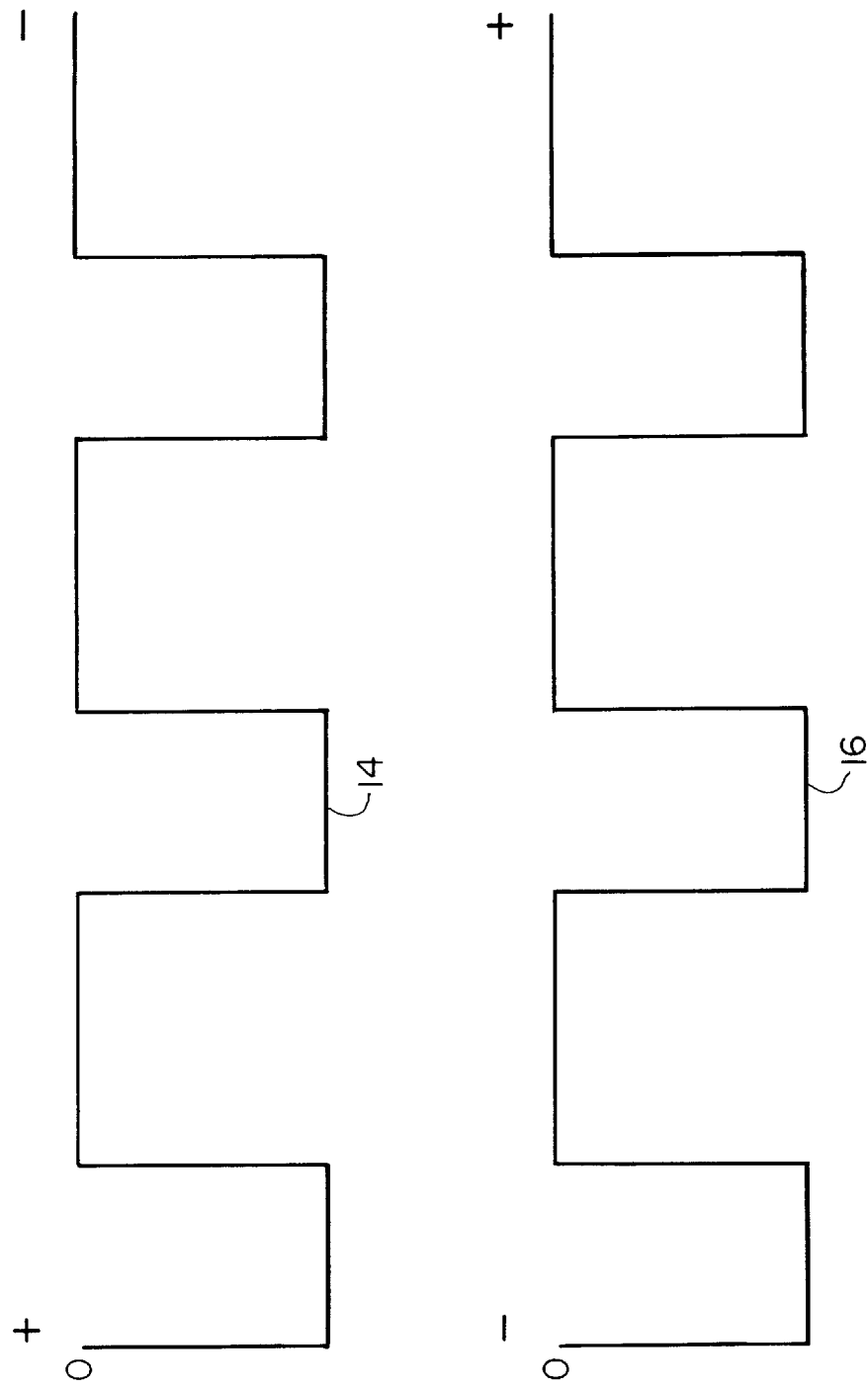
FIGS. 3A and 3B show two monopolar pulse trains with reversible electrode polarity and timing diagram illustrating negative pulse polarity.

The controller 3 of FIG. 7 generates square wave pulse trains of current between the positive electrode 2 and the negative electrodes 4. Because the physiology of different patients will affect their sensitivity to electric current, the circuit of FIG. 7 can adjust the basic parameters of the pulse current train between the electrodes 2,4. One important parameter of the pulse current train is the pulse polarity, which significantly influences the inhibition of the uterine contractions. For example, a positive pulse polarity can be established between the positive and negative electrodes 2,4 by changing the polarity from zero for negative-to-positive as shown in FIGS. 2A and 2B about a zero milliampere center line. In contrast, the circuit of the FIG. 7 can also provide negative pulse polarity in which the polarity changes from zero or positive-to-negative as shown in FIGS. 3A and 3B about a zero milliampere center line.

Figure 4:
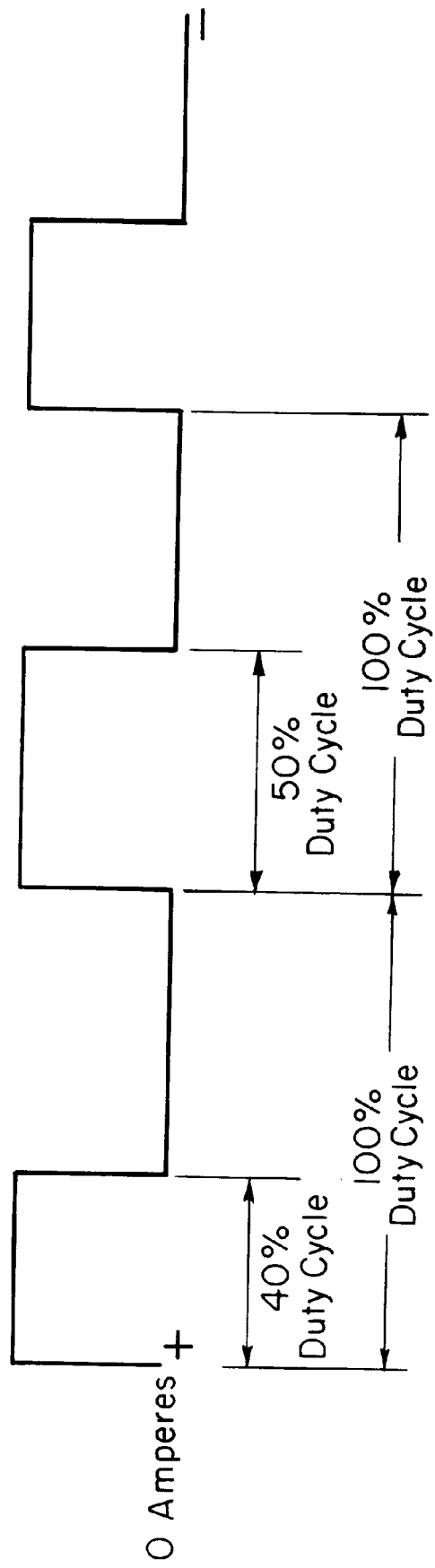
FIG. 4 is a timing diagram of a pulse produced by the apparatus of the present invention illustrating positive polarity and monopolar pulses with different duty cycles of the invention.

Since the circuit of FIG. 7 is also provided with a pulse width control 36 the duty cycle of the pulse current trains can also be adjusted. This is particularly advantageous since changes in pulse duration are known to greatly influence the effect upon the muscle. Very short pulse widths predominantly influence nerves while slightly longer pulse widths influence the muscle. A pulse width that is equal to or less than a 50% duty cycle, 50% of the time the current is on and 50% of the time the current is off, is shown in FIG. 4. This pulse width has been shown to inhibit muscle activity. Alternatively, a stimulatory effect can be obtained by appropriate selection of the duty cycles.

Figure 8:
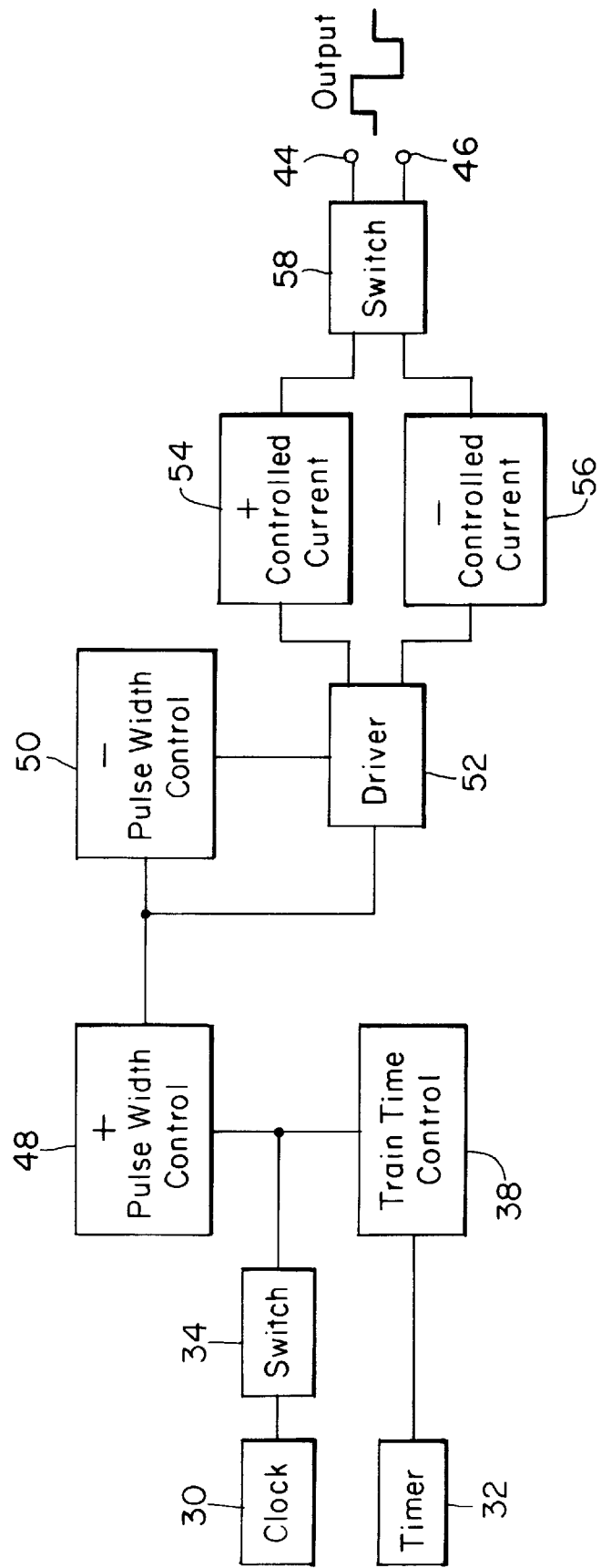
FIG. 8 shows a block diagram of a circuit of the invention for producing the pulses shown in FIGS. 2 to 6.

FIG. 8 illustrates a second embodiment of the muscle controller circuit 3. This second embodiment is capable of producing bi-polar pulse current trains. This circuit includes a clock 30 that connects to a switch 34 that allows for the activation of the controller 3. The timer 32 connects to the train on time control 38 that determines the amount of time that current flows between the electrodes. The switch 34 connects to a positive pulse width control 48, the timer on circuit 32 and train on time control 38. The output of the positive pulse width control 48 is connected to a negative pulse width control 50. Both of the pulse width controls 48,50 are connected to driver 52. The driver 52 drives a positive controlled current unit 54 and a negative controlled current unit 56. Both of these units 54 and 56 are connected to a switch 58 for controlling the polarity of the electrodes attached to the output terminals 44 and 46.

FIGS. 5A and 5B show the bi-polar current pulses that can be generated by the second embodiment of the controller shown in FIG. 8. Specifically, half of the pulse has a positive polarity 18A while a subsequent half has a negative polarity 18B. Activation of the switch 58 can cause the reversal of the electrode polarity, FIG. 5B, so that half of the 20a pulse is positive and half negative 20b. Here, the same pulse train is generated except that it is provided to the negative electrodes instead of the positive electrode.

Figure 6A:
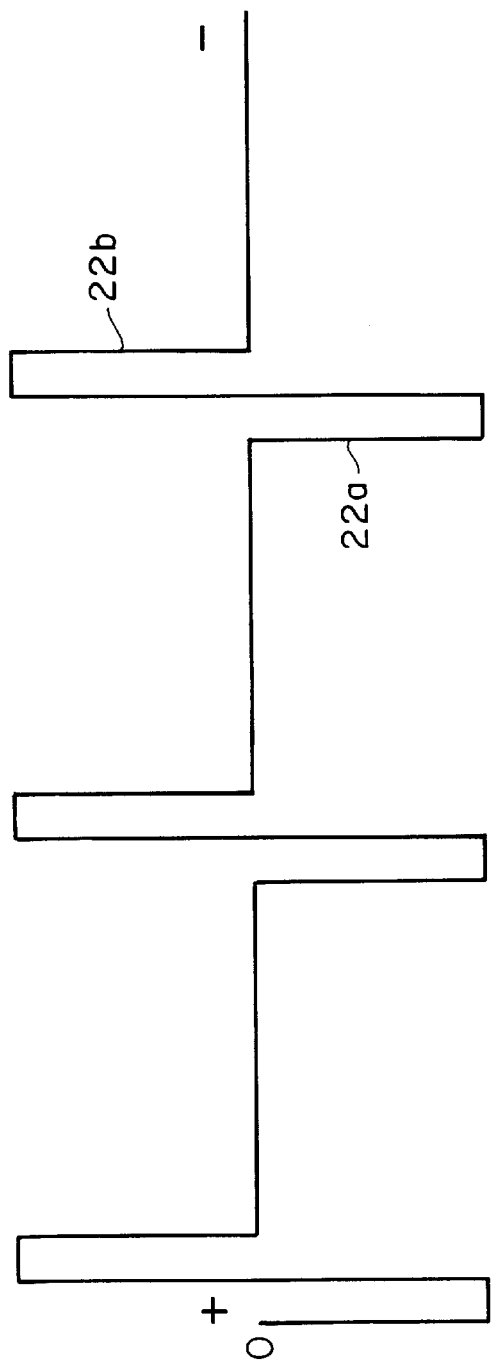
FIGS. 6A and 6B is a timing diagram of a pulse illustrating reversible electrode polarity and reversed bipolar pulses (negative-to-positive-to-negative) of the invention.
Figure 6B:
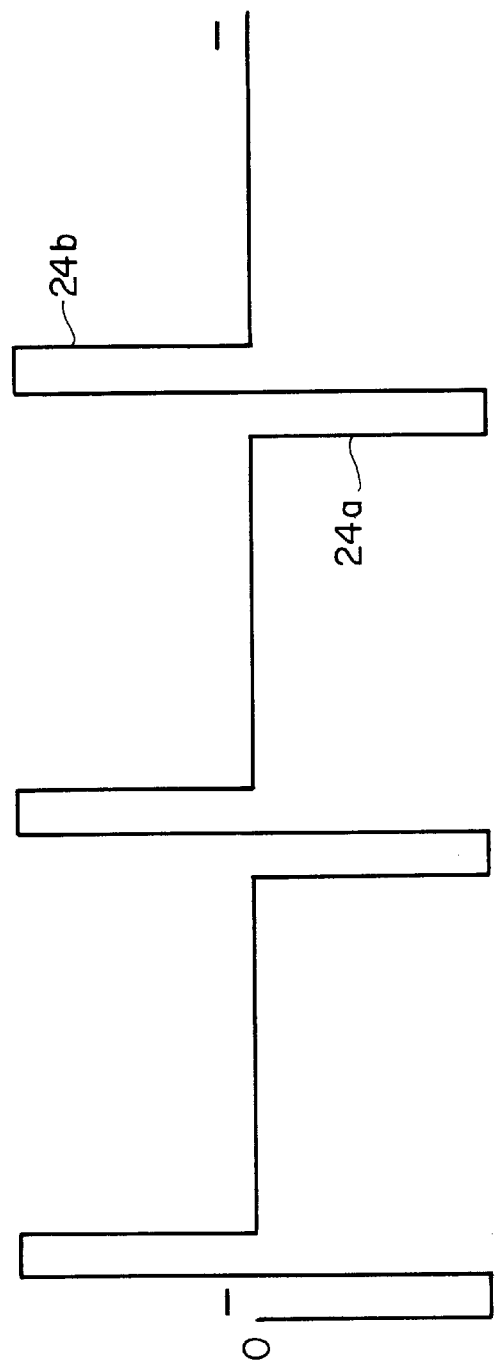

Alternatively, as shown in FIG. 6A, the circuit of FIG. 8 can also control the bi-polar circuit pulses so that the initial pulse is negative 22A and followed by a positive pulse 22B. The polarity of the pulses in FIG. 6B have a reversed polarity so that there is an initially negative pulse 24A then a positive pulse 24B.

Depending on the individuals physiology, various depths of penetration will be needed to affect the muscle of interest. For this reason, the frequencies are variable in the range of zero to 50 pulses per second, pps. In addition, the sensitivity of the muscle of interest varies with the individual, thus the amount of time needed for the current to affect the muscle will vary. The present invention can vary the amount of time that the current is applied. This is varied from zero to continuously with the timer circuit 32 of FIGS. 7 and 8 so that current is applied to the muscle of interest only for the amount of time needed for the maximal therapeutic effect.

Figure 10:
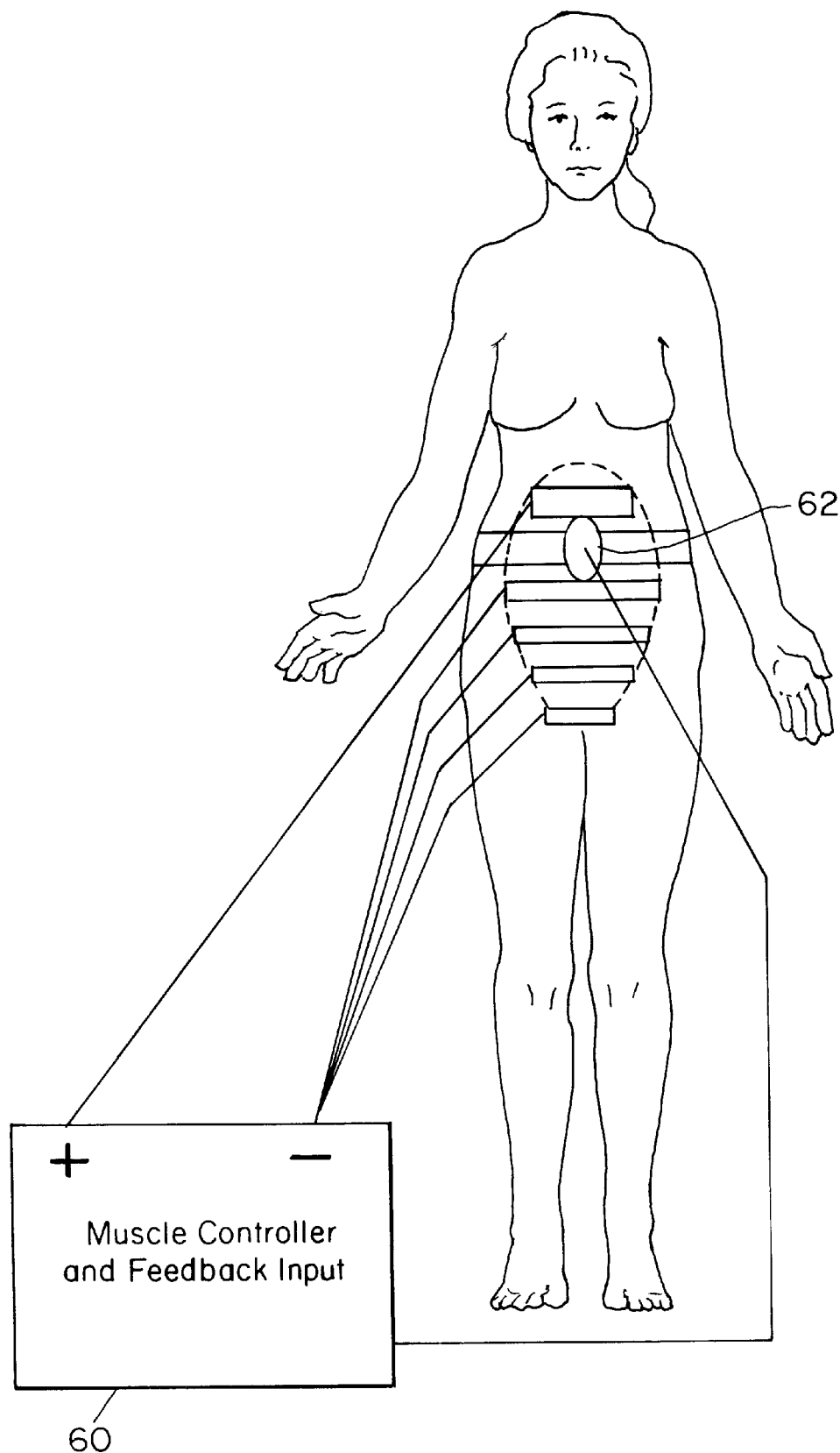
FIG. 10 is a schematic view of the transcutaneous uterine muscle/nerve controller/feedback apparatus and electrodes attached over the uterus of a human body of the present invention including feedback input control of the output.

FIG. 10 shows another embodiment of the invention which a plurality of electrodes 2,4 are positioned over the uterus 1 of a female. One difference from previous embodiments is the provision of positive or negative feedback control of the current to the electrodes 2,4. A uterine contraction monitor 62 is positioned to monitor contractions of the uterus and provide an electrical signal to a controller and feedback input unit 60 in response to these contractions. For example, when uterine smooth muscle activity is detected, the controller and feedback input unit 60 is activated for either positive or negative feedback input to the muscle controller 60.

Figure 9:
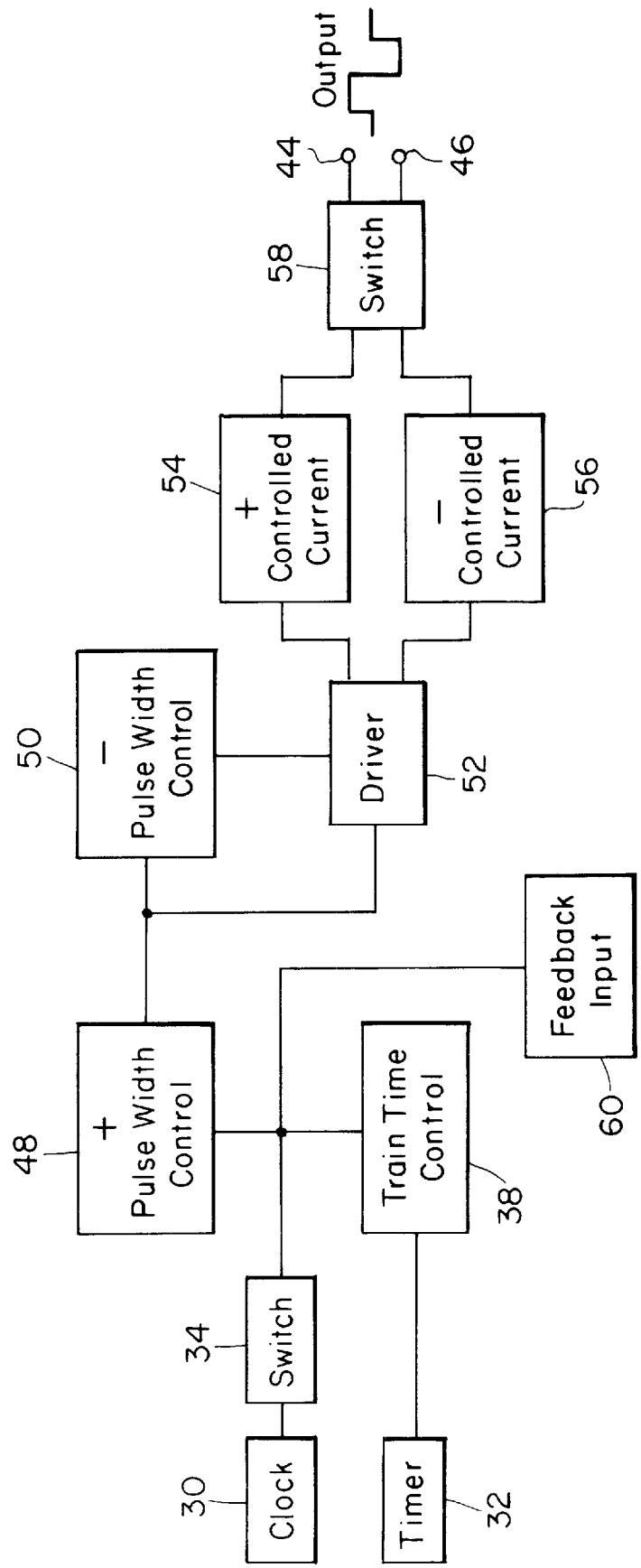
FIG. 9 shows a block diagram of a circuit of the invention for producing the pulses shown in FIGS. 2 to 6 including feedback input control of the output.

FIG. 9 is a block diagram of the controller and feedback input unit 60. This is substantially similar to the second embodiment of FIG. 8 in operation except that feedback is received through the feedback input 63. Therefore, the controller can generate positive or negative feedback in response to muscle activity. Accordingly, the above-described controller of this invention in its various embodiments may be used to inhibit, decrease, or stimulate, increase, smooth muscle activity by changing the dynamics of a current pulse train provided between electrodes 2,4 positioned on the patient.

Although the description above contains many specificities, these should not be construed as limiting the scope of the invention but merely providing illustrations of some of the presently preferred embodiments of this invention. For example, the muscle/nerve controller can be used not only on the smooth muscle of the uterus to inhibit or stimulate the contractions of labor but can be used on the smooth muscle of the bladder, tracheobronchial tree, gastrointestinal track, etc. Thus, the scope of the invention should be determined by the appended claims and their legal equivalents rather than by the examples given.

I claim:

1. A method for inhibiting uterine contractions, comprising:

determining the presence of uterine contractions; and establishing electrical current flow along an anterior side of an abdomen of a patient to affect the contractions.

2. A method as described in claim 1, further comprising:

placing electrodes on the abdomen of the patient; and establishing the current flow between the electrodes.

3. A method as described in claim 2, further comprising placing plural electrodes of a same polarity on the abdomen.

4. A method as claimed in claim 1, further comprising:

placing an electrode of a first polarity on the abdomen;

placing plural electrodes of a second polarity on the abdomen; and establishing the current flow between the first polarity electrode and the plural second polarity electrodes.

5. A method as described in claim 1, further comprising selecting the current flow to attenuate the uterine contractions.

6. A method as described in claim 1, wherein the step of establishing the electrical current flow comprises generating constant amplitude current pulses.

7. A method as described in claim 1, further comprising:

detecting uterine contraction with a sensor; and controlling the electrical current flow in response to the uterine contractions.

8. A uterine contraction inhibiting device comprising:

electrodes for being placed on an anterior side of an abdomen of a patient; and a generator for establishing electrical current between the electrodes to affect uterine contractions of the patient; and a sensor for detecting the uterine contractions, the detection being used to control the electrical current of the generator in response to the detected contractions.

9. A device as described in claim 8, wherein the generator generates constant current electrical pulses.

10. A device as described in claim 8, wherein the electrodes comprise:

a first polarity electrode; and at least one second polarity electrode.

11. A method for affecting uterine contractions comprising:

determining the presence of uterine contractions; and establishing electrical current flow along an anterior side of a uterus of a patient to affect the contractions.

12. The method of claim 11 further comprising:

placing electrodes on an anterior side of a uterus of the patient.

13. The method of claim 11 further comprising:

placing electrodes on an abdomen of the patient; and establishing current flow between the electrodes.

14. The method of claim 11 wherein the step of establishing the electrical current flow comprising generating constant amplitude current pulses.

15. The method of claim 11 wherein the determining step comprises determining the presence of uterine contractions with a sensor.

16. A method of affecting uterine contractions comprising:

applying electrodes to a patient anterior to the patient's uterus; and establishing electrical current flow along an anterior side of the uterus.

17. The method of claim 16, further comprising:

placing electrodes on an anterior side of a uterus of the patient.

18. The method of claim 16 further comprising:

placing electrodes on an abdomen of the patient; and establishing current flow between the electrodes.

19. The method of claim 16 wherein the step of establishing the electrical current flow comprises generating constant amplitude current pulses.

20. The method of claim 16 wherein the determining step comprises determining the presence of uterine contractions with a sensor.

* * * * *